(12) United States Patent
Weber et al.

(10) Patent No.: US 7,250,548 B2
(45) Date of Patent: Jul. 31, 2007

(54) ABSORBENT ARTICLE WITH TEMPERATURE CHANGE MEMBER DISPOSED ON THE OUTER COVER AND BETWEEN ABSORBENT ASSEMBLY PORTIONS

(75) Inventors: Shirlee A. Weber, Neenah, WI (US); Christopher P. Olson, Neenah, WI (US); Andrew M. Long, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/955,534

(22) Filed: Sep. 29, 2004

(65) Prior Publication Data

US 2006/0069363 A1    Mar. 30, 2006

Related U.S. Application Data

(63) Continuation-in-part of application No. 10/462,166, filed on Jun. 16, 2003.

(51) Int. Cl.
*A61F 13/49* (2006.01)

(52) U.S. Cl. .................... 604/361; 604/367

(58) Field of Classification Search ........ 340/603–605, 340/618, 622, 501, 606; 604/358–402
See application file for complete search history.

(56) References Cited

U.S. PATENT DOCUMENTS

| | | | |
|---|---|---|---|
| 2,907,173 A | 10/1959 | Robbins | |
| 3,375,827 A | 4/1968 | Bletzinger et al. | |
| 3,849,241 A | 11/1974 | Butin et al. | |
| 3,918,454 A | 11/1975 | Korodi et al. | |
| 4,029,100 A | 6/1977 | Karami | |
| 4,100,324 A | 7/1978 | Anderson et al. | |
| 4,231,370 A | 11/1980 | Mroz et al. | |
| 4,375,448 A | 3/1983 | Appel et al. | |
| 4,507,121 A | 3/1985 | Leung et al. | |
| 4,578,066 A * | 3/1986 | O'Connor | 604/366 |
| 4,604,313 A | 8/1986 | McFarland et al. | |
| 4,653,491 A * | 3/1987 | Okada et al. | 128/886 |
| 4,655,757 A | 4/1987 | McFarland et al. | |
| 4,663,220 A | 5/1987 | Wisneski et al. | |
| 4,666,647 A | 5/1987 | Enloe et al. | |
| 4,673,403 A | 6/1987 | Lassen et al. | |
| 4,699,619 A | 10/1987 | Bernardin | |
| 4,704,116 A | 11/1987 | Enloe | |
| 4,761,258 A | 8/1988 | Enloe | |
| 4,773,905 A | 9/1988 | Molee et al. | |
| 4,781,962 A * | 11/1988 | Zamarripa et al. | 428/138 |
| 4,834,733 A | 5/1989 | Huntoon et al. | |

(Continued)

FOREIGN PATENT DOCUMENTS

CA    1 057 459 A    7/1979

(Continued)

OTHER PUBLICATIONS

Definitions for "gap" from various online dictionaries.*

(Continued)

*Primary Examiner*—Tatyana Zalukaeva
*Assistant Examiner*—Laura C Hill
(74) *Attorney, Agent, or Firm*—Senniger Powers (57) ABSTRACT

An absorbent article may define a front region, a rear region, and a crotch region intermediate the front and rear regions. The article may include an outercover, a liner and an absorbent assembly front portion disposed intermediate the outercover and the liner in the front region. The article may also include an absorbent assembly rear portion disposed intermediate the outercover and the liner in the rear region and at least partially spaced from the absorbent assembly front portion to provide a first gap. The article further includes a temperature change member disposed in the first gap.

25 Claims, 6 Drawing Sheets

U.S. PATENT DOCUMENTS

| | | |
|---|---|---|
| 4,940,464 A | 7/1990 | Van Gompel et al. |
| 4,960,477 A | 10/1990 | Mesek |
| 5,046,272 A | 9/1991 | Vogt et al. |
| 5,104,116 A | 4/1992 | Pohjola |
| 5,114,781 A | 5/1992 | Morman |
| 5,116,662 A | 5/1992 | Morman |
| 5,147,343 A | 9/1992 | Kellenberger |
| 5,178,139 A * | 1/1993 | Angelillo et al. ........... 607/114 |
| 5,197,958 A | 3/1993 | Howell |
| 5,213,881 A | 5/1993 | Timmons et al. |
| 5,224,405 A | 7/1993 | Pohjola |
| 5,226,992 A | 7/1993 | Morman |
| 5,236,428 A * | 8/1993 | Zajaczkowski ........ 604/385.26 |
| 5,266,592 A | 11/1993 | Grub et al. |
| 5,277,180 A | 1/1994 | Angelillo et al. |
| 5,284,703 A | 2/1994 | Everhart et al. |
| 5,286,543 A * | 2/1994 | Ungpiyakul et al. ..... 428/32.24 |
| 5,286,770 A | 2/1994 | Bastioli et al. |
| 5,348,750 A | 9/1994 | Greenberg |
| 5,350,624 A | 9/1994 | Georger et al. |
| 5,387,210 A * | 2/1995 | Murakami .................. 604/396 |
| 5,425,725 A | 6/1995 | Tanzer et al. |
| 5,460,623 A | 10/1995 | Emenaker et al. |
| 5,484,430 A | 1/1996 | Osborn, III |
| 5,486,166 A | 1/1996 | Bishop et al. |
| 5,490,846 A | 2/1996 | Ellis et al. |
| 5,494,622 A | 2/1996 | Heath et al. |
| 5,575,785 A | 11/1996 | Gryskiewicz et al. |
| 5,601,542 A | 2/1997 | Melius et al. |
| 5,607,760 A | 3/1997 | Roe |
| 5,609,587 A | 3/1997 | Roe |
| 5,645,542 A | 7/1997 | Anjur et al. |
| 5,649,914 A | 7/1997 | Glaug et al. |
| 5,649,919 A * | 7/1997 | Roessler et al. ....... 604/385.29 |
| 5,658,268 A | 8/1997 | Johns et al. |
| 5,681,289 A | 10/1997 | Wilcox et al. |
| 5,681,298 A | 10/1997 | Brunner et al. |
| 5,702,376 A | 12/1997 | Glaug et al. |
| 5,702,377 A | 12/1997 | Collier, IV et al. |
| 5,766,389 A | 6/1998 | Brandon et al. |
| 5,769,835 A | 6/1998 | Fell et al. |
| 5,797,892 A | 8/1998 | Glaug et al. |
| 5,814,035 A | 9/1998 | Gryskiewicz et al. |
| 5,861,440 A | 1/1999 | Gohla et al. |
| 5,863,288 A | 1/1999 | Baker |
| 5,883,028 A | 3/1999 | Morman et al. |
| 5,885,264 A | 3/1999 | Matsushita |
| 5,900,109 A | 5/1999 | Sanders et al. |
| 5,913,851 A | 6/1999 | Gryskiewicz et al. |
| 5,921,974 A | 7/1999 | Kikuchi |
| 5,935,118 A | 8/1999 | Gryskiewicz et al. |
| 5,964,743 A | 10/1999 | Abuto et al. |
| 5,994,614 A | 11/1999 | Wada et al. |
| 6,126,648 A | 10/2000 | Keck et al. |
| 6,159,591 A | 12/2000 | Beihoffer et al. |
| 6,162,961 A | 12/2000 | Tanner et al. |
| 6,180,847 B1 | 1/2001 | Ahr et al. |
| 6,221,460 B1 | 4/2001 | Weber et al. |
| 6,231,557 B1 | 5/2001 | Krautkramer et al. |
| 6,245,410 B1 | 6/2001 | Hahnle et al. |
| 6,306,412 B1 | 10/2001 | Crotty et al. |
| 6,330,735 B1 | 12/2001 | Hahn et al. |
| 6,362,389 B1 | 3/2002 | McDowall et al. |
| 6,414,035 B1 | 7/2002 | Vargas Munita et al. |
| 6,437,212 B1 | 8/2002 | La Fortune |
| 6,461,086 B1 | 10/2002 | Milanowski et al. |
| 6,552,245 B1 | 4/2003 | Roessler et al. |
| 6,582,413 B2 | 6/2003 | Krautkramer et al. |
| 6,627,786 B2 | 9/2003 | Roe et al. |
| 6,642,427 B2 * | 11/2003 | Roe et al. .................... 604/361 |
| 6,645,190 B1 | 11/2003 | Olson et al. |
| 6,657,100 B1 | 12/2003 | Underhill et al. |
| 6,867,343 B2 | 3/2005 | La Fortune |
| 7,002,055 B2 | 2/2006 | Long et al. |
| 2002/0095126 A1 * | 7/2002 | Inoue et al. ................. 604/361 |
| 2002/0169427 A1 * | 11/2002 | Roe et al. .................... 604/361 |
| 2003/0130636 A1 | 7/2003 | Brock et al. |
| 2003/0147941 A1 | 8/2003 | Koenig et al. |
| 2003/0199845 A1 | 10/2003 | Roe et al. |
| 2004/0015143 A1 | 1/2004 | Underhill et al. |
| 2004/0030310 A1 | 2/2004 | Roe et al. |
| 2004/0082928 A1 | 4/2004 | Pesce et al. |
| 2004/0113801 A1 * | 6/2004 | Gustafson et al. .......... 340/604 |
| 2004/0185093 A1 | 9/2004 | Szmczak |
| 2004/0254549 A1 * | 12/2004 | Olson et al. ................. 604/361 |
| 2004/0254550 A1 * | 12/2004 | Huang et al. ............... 604/361 |
| 2005/0096623 A1 | 5/2005 | Nhan et al. |
| 2005/0137085 A1 | 6/2005 | Zhang et al. |
| 2005/0148961 A1 | 7/2005 | Sosalla et al. |
| 2006/0004336 A1 | 1/2006 | Zhang et al. |
| 2006/0005919 A1 | 1/2006 | Schewe et al. |
| 2006/0069363 A1 | 3/2006 | Weber et al. |

FOREIGN PATENT DOCUMENTS

| | | |
|---|---|---|
| CA | 2 074 649 A1 | 2/1993 |
| CA | 1 315 488 C | 4/1993 |
| CA | 2 208 888 A1 | 6/1996 |
| CA | 2 208 891 A1 | 6/1996 |
| CA | 2 228 043 C | 2/1997 |
| CA | 2 228 130 C | 2/1997 |
| CA | 2 312 840 A1 | 6/1999 |
| CA | 2 183 238 C | 2/2001 |
| CA | 2 391 936 A1 | 2/2001 |
| CA | 2 441 135 A1 | 10/2002 |
| CA | 2 467 968 A1 | 6/2003 |
| CA | 2 461 275 A1 | 9/2004 |
| DE | 36 08 114 A1 | 9/1987 |
| DE | 197 45 878 C1 | 12/1998 |
| EP | 0 203 715 A2 | 12/1986 |
| EP | 0 217 032 | 4/1987 |
| EP | 0 339 461 A1 | 11/1989 |
| EP | 0 217 032 B1 | 2/1992 |
| EP | 0 538 535 A1 | 4/1993 |
| EP | 0 704195 A2 * | 4/1996 |
| JP | 2003-020568 A | 1/2003 |
| WO | WO 96/19168 A2 | 6/1996 |
| WO | WO 96/19172 A1 | 6/1996 |
| WO | WO 98/29079 A1 | 7/1998 |
| WO | WO 00/37009 | 6/2000 |
| WO | WO 00/37009 A2 | 6/2000 |
| WO | WO 01/88245 | 11/2001 |
| WO | WO 01/88245 A2 | 11/2001 |
| WO | WO 02/091968 | 11/2002 |
| WO | WO 02/091968 A2 | 11/2002 |
| WO | WO 03/047641 A1 | 6/2003 |
| WO | WO 03/051254 A2 | 6/2003 |
| WO | WO 03/051258 A1 | 6/2003 |
| WO | WO 03/053481 A1 | 7/2003 |
| WO | WO 03/57109 A1 | 7/2003 |
| WO | WO 03/057122 A1 | 7/2003 |
| WO | WO 2004/022115 A1 | 3/2004 |
| WO | WO 2005/004771 A1 | 1/2005 |

OTHER PUBLICATIONS

International Search Report for PCT/US2004/004066, dated Jul. 27, 2004, 8 pages.

International Search Report for PCT/US2005/027230 dated Nov. 28, 2005, 4 pages.

* cited by examiner

ABSORBENT ARTICLE WITH TEMPERATURE CHANGE MEMBER DISPOSED ON THE OUTER COVER AND BETWEEN ABSORBENT ASSEMBLY PORTIONS

FIELD OF THE INVENTION

The present invention relates to absorbent articles that include a temperature change member. More specifically, the invention relates to an absorbent article such as training pants that provides the wearer with a noticeable temperature change sensation upon urination. Such articles can facilitate the toilet training process.

BACKGROUND OF THE INVENTION

Absorbent articles such as disposable diapers and training pants are useful to absorb and contain body wastes. These products have developed to the extent that urine is quickly drawn and retained away from the wearer's skin so that the wearer remains relatively dry and comfortable. Although improved performance of disposable absorbent products enhances wearer dryness and comfort, it can reduce the wearer's ability to notice or recognize when urination occurs, especially if the wearer's attention is distracted by an activity. This is not conducive to toilet training because an important step in the early stages of toilet training is the ability to recognize when urination occurs.

In an attempt to enhance a child's recognition of when urination occurs, training pants have been designed with temperature change members that provide a temperature change sensation upon urination. For example, a temperature change substance, such as endothermic particles, may be contained within a liquid permeable cover that is strategically located on the absorbent article. Upon urination, urine flows through the liquid permeable cover, contacts the temperature change substance and cools down.

Unfortunately, in certain circumstances where the temperature change substance generally is located above the main absorbent assembly, the temperature change substance may not be fully effective as the urine can rinse through the temperature change member and be quickly absorbed into the absorbent assembly. As such, in those instances there may not be a distinct indication of urination.

Further, in configurations where the temperature change member is disposed above the absorbent assembly it can render the article relatively bulky.

Thus, there is a need or desire for an absorbent article with a temperature change member that is arranged to contact urine effectively during urination so as to provide a wearer with a distinct temperature change sensation, and hence a distinct signal that urination has occurred.

It is also desirable for such an absorbent article to be relatively thin so as to enhance the underwear-like perception of the garment.

SUMMARY OF THE INVENTION

In one aspect, the present invention is directed to an absorbent article defining a front region, a rear region and a crotch region intermediate the front and rear regions. The absorbent article includes a liquid impermeable outercover and a liquid permeable bodyside liner. The article also includes an absorbent assembly front portion disposed intermediate the outercover and the liner in the front region. The article further includes an absorbent assembly rear portion disposed intermediate the outercover and the liner in the rear region. The absorbent assembly rear portion is at least partially spaced from the absorbent assembly front portion to provide a first gap. The article further also includes a temperature change member containing a temperature change substance disposed in the first gap intermediate the outer cover and the bodyside liner.

In another aspect, the present invention is directed to an absorbent article defining a front region, a rear region and a crotch region intermediate the front and rear regions. The absorbent article includes a liquid impermeable outer cover and an absorbent assembly front portion disposed on the outer cover in the front region. The article also includes an absorbent assembly rear portion disposed on the outer cover in the rear region and at least partially spaced from the absorbent assembly front portion to provide a first gap. The article further includes a temperature change member disposed on the outer cover in the first gap.

The absorbent article can further define a front waist edge and a rear waist edge. The absorbent assembly front portion may be spaced from the front waist edge by a second gap, and the absorbent assembly rear portion may be spaced from the rear waist edge by a third gap. The length of the absorbent assembly front portion can be the same as the length of the absorbent assembly rear portion, and the length of the first gap between the absorbent assembly front portion and the absorbent assembly rear portion is the same as the sum of: (a) the length of the second gap between the absorbent assembly front portion and the front waist edge, and (b) the length of the third gap between the absorbent assembly rear portion and the rear waist edge. Such a configuration of the absorbent assembly front portion, the absorbent assembly rear portion and the temperature change member facilitates continuous production of absorbent articles according to the present invention.

Thus, the present invention is directed to an absorbent article such as a training pant, a diaper or an incontinence garment that may include a temperature change member positioned and adapted to create a distinct temperature change sensation upon urination, thereby enhancing the wearer's ability to recognize that urination has occurred. The broad scope of the applicability of the present invention will become apparent to those of skill in the art from the details given below. Moreover, the detailed description presented below is given by way of example only, and various modifications within the scope of the invention will be apparent to those of skill in the art.

DEFINITIONS

As used herein, the term "attached" refers to the joining, adhering, bonding, connecting, or the like, of two elements. Two elements will be considered to be attached together when they are integral with one another, or attached directly to one another or indirectly to one another, such as when each is directly bonded to intermediate elements.

As used herein, the term "bonded" refers to the joining, adhering, connecting, attaching or the like, of two elements. Two elements will be considered to be bonded together when they are bonded directly to one another or indirectly to one another, such as when each is directly bonded to intermediate elements.

As used herein, the term "comprising" is intended to be inclusive or open-ended, and is not intended to exclude additional elements that do not prevent operation of the invention.

As used herein, the term "disposable", when used to describe articles such as garments, means an article that is designed to be discarded after a limited use rather than being laundered or otherwise restored for use.

As used herein, the term "disposed" and variations thereof is intended to mean that one element can be integral with another element, or that one element can be a separate structure attached to or placed with another element or placed near another element.

As used herein, the term "liquid impermeable", when used to describe a layer or multi-layer laminate, means that a liquid, such as urine, will not pass through the layer or laminate, under ordinary use conditions, in a direction generally perpendicular to the plane of the layer or laminate at the point of liquid contact, and "liquid permeable" means a layer or laminate that is not liquid impermeable.

As used herein, the term "member" when used in the singular can have the dual meaning of a single element or a plurality of elements.

As used herein, the term "non-woven material" means a material that is formed without the aid of a textile weaving or knitting process.

As used herein, the term "superabsorbent" refers to a water-swellable, water-insoluble organic or inorganic material capable, under the most favorable conditions, of absorbing at least about fifteen times its weight and, more suitably, at least about thirty times its weight in an aqueous solution containing 0.9 weight percent sodium chloride. The superabsorbent materials can be natural, synthetic or modified natural polymers and materials, or a combination of such materials. In addition, the superabsorbent materials can be inorganic materials, such as silica gels, or organic compounds such as cross-linked polymers.

These terms may be defined with additional language in the remaining portions of the specification.

DETAILED DESCRIPTION OF THE INVENTION

Figure 1:
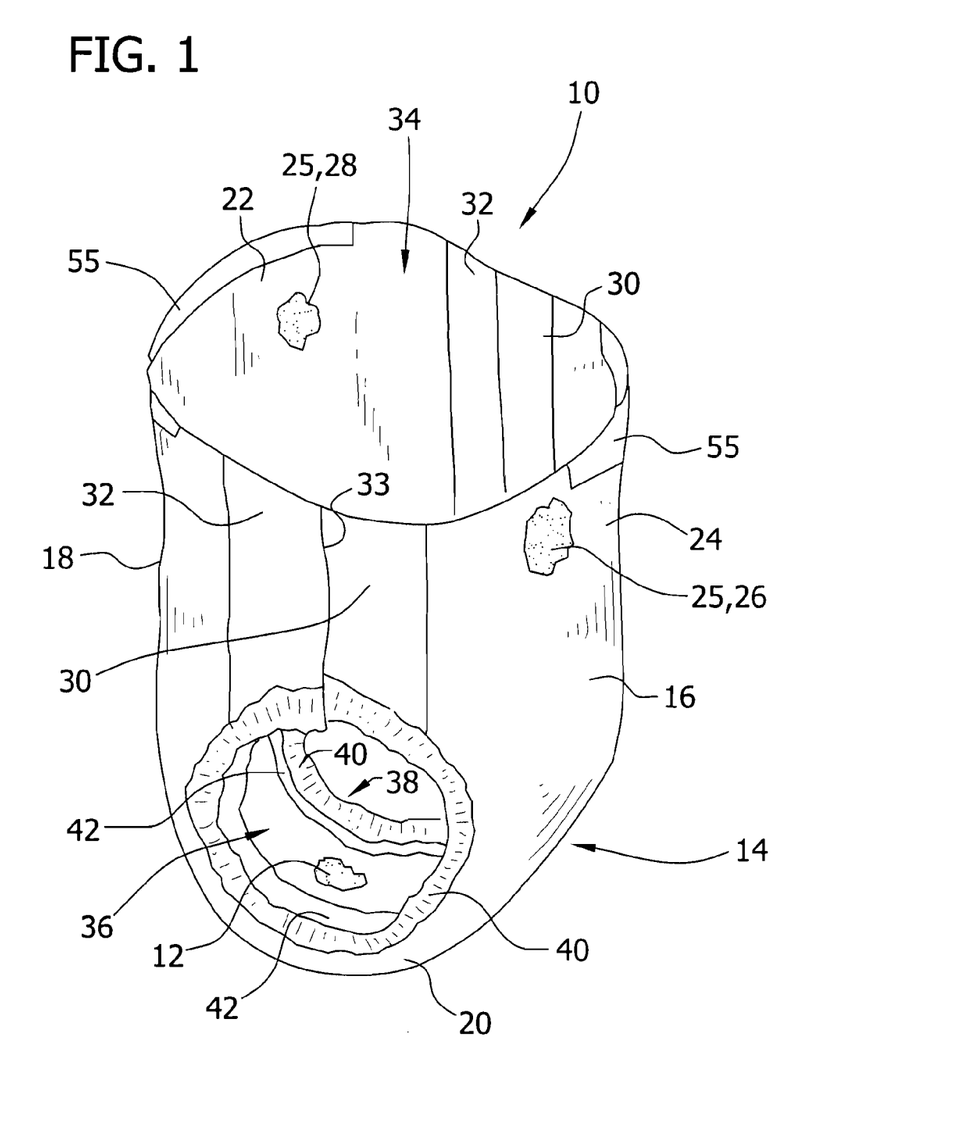
FIG. 1 representatively illustrates a perspective view of an absorbent article according to aspects of the present invention, with portions cut away to show underlying features.
Figure 2:
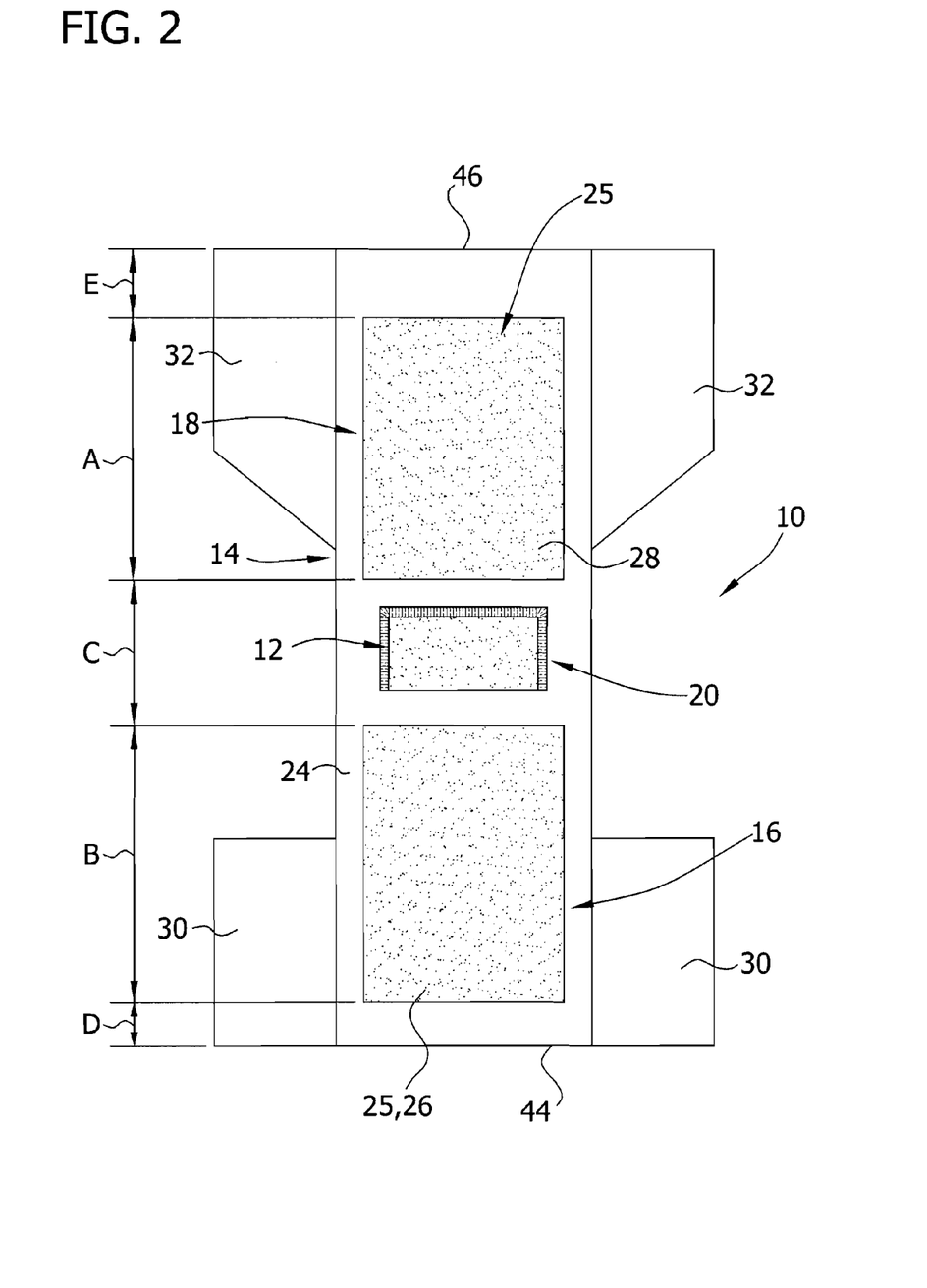
FIG. 2 representatively illustrates a top view of an absorbent article according to aspects of the present invention at an intermediate stage of assembly and in a flat and stretched condition, with certain components omitted for clarity.
Figure 7:
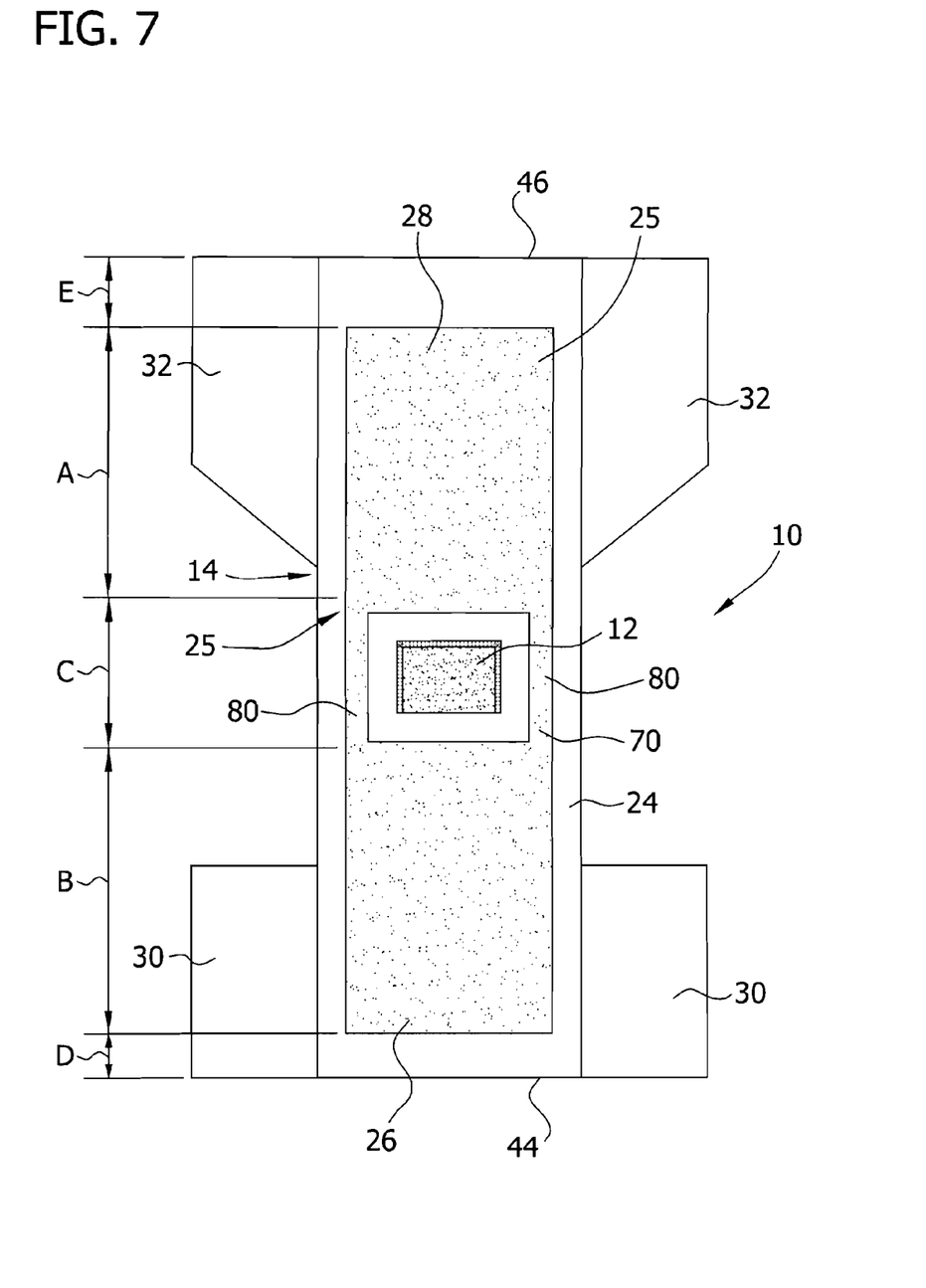
FIG. 7 representatively illustrates a top view of an absorbent article according to an alternative aspect of the present invention at an intermediate stage of assembly and in a flat and stretched condition, with certain components omitted for clarity.

With reference to FIGS. 1, 2 and 7, an absorbent article 10 is shown for purposes of illustration as disposable training pants for use by a child. The training pants 10 are illustrated in an operative, fastened condition in FIG. 1, and in FIGS. 2 and 7 the training pants are shown in an intermediate stage of assembly, in a flat and stretched condition, with certain components omitted for clarity. The training pants 10 include a temperature change member 12 that is positioned and adapted to create a distinct temperature change sensation upon urination, thereby to enhance the wearer's ability to recognize when urination is occurring. The invention may also be embodied in other types of absorbent articles such as, for example, diapers or adult incontinence products.

By way of illustration only, various materials and methods for constructing training pants such as the pants 10 of the various aspects of the present invention are disclosed in PCT Patent Application WO 00/37009 published on Jun. 29, 2000 in the name of A. Fletcher et al.; U.S. Pat. No. 4,940,464 issued on Jul. 10, 1990 to Van Gompel et al.; U.S. Pat. No. 5,766,389 issued on Jun. 16, 1998 to Brandon et al.; and U.S. Pat. No. 6,645,190 issued on Nov. 11, 2003 to Olson et al., the contents of which are incorporated herein by reference.

The training pants 10 include a chassis 14, and define first and second end regions, e.g., a front region 16, and a rear region 18. The pants 10 also define an intermediate region, e.g., a crotch region 20, intermediate and interconnecting the front and rear regions 16 and 18. The chassis 14 includes a liquid permeable bodyside liner 22 for contacting a wearer's body, and a liquid impermeable outer cover 24 for contacting the wearer's clothing. An absorbent assembly 25, which can include an absorbent assembly front portion 26 and an absorbent assembly rear portion 28, can be disposed on the chassis 14 intermediate the bodyside liner 22 and the outer cover 24. The various components of the pants 10 described herein may be attached to one another in a variety of ways as are known to those skilled in the art and include adhesives, ultrasonic bonding, thermal bonding, pressure bonding or other suitable attachment means, or combinations thereof.

In the various aspects of the present invention, the absorbent assembly 25 and the temperature change member 12 may be arranged to maximize the performance of the temperature change member. For example, the absorbent assembly front portion 26 may be at least partially spaced from the absorbent assembly rear portion 28 to provide a first gap C and the temperature change member 12 may be disposed between the front and rear absorbent assemblies 26 and 28, as representatively illustrated in FIGS. 2 and 7.

The training pants 10 can have transversely opposed, front side panel portions 30 attached to the chassis 14 in the front region 16 of the pants 10, and transversely opposed, rear side panel portions 32 attached to the chassis 14 in the rear region 18 of the pants 10. The front and rear side panel portions 30 may be refastenably attachable to one another by a fastening system 33. The absorbent chassis 14, side panels 30 and 32, and the fastening system 33 together define refastenable pants having a waist opening 34, and a pair of leg openings 36 and 38. Alternatively, the front side panel portions 30 may be permanently bonded to the rear side panel portions 32 by non-refastenable seams, which may be formed by any suitable means such as, for example, ultrasonic sealing, adhesive bonding, heat sealing, adhesive coated tapes, or the like. As mentioned above, the side panels 30 and 32 may be separate members that are attached to the chassis 14 or alternatively they may be formed integrally with the chassis 14, for example as integral parts of the outer cover 24 and/or liner 22.

Suitable elastic materials for forming the front side panels 30 and the rear side panels 32, as well as processes for incorporating elastic side panels into training pants, are described in U.S. Pat. No. 4,940,464 issued on Jul. 10, 1990 to Van Gompel et al.; U.S. Pat. No. 5,224,405 issued on Jul. 6, 1993 to Pohjola; U.S. Pat. No. 5,104,116 issued on Apr. 14, 1992 to Pohjola; and U.S. Pat. No. 5,046,272 issued on Sep. 10, 1991 to Vogt et al., the contents of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued on May 5, 1987 to Wisneski et al.; U.S. Pat. No. 5,226,992 issued on Jul. 13, 1993 to Morman; European Patent Application EP 0 217 032 published on Apr. 8, 1987 in the name of Taylor et al.; and PCT Patent Application WO 01/88245 in the name of Welch et al., the contents of which are incorporated herein by reference. As is known in the art, the side panels 30 and 32 may include elastic material or stretchable but inelastic material.

The fastening system 33 may include any refastenable fasteners suitable for absorbent articles, such as adhesive fasteners, cohesive fasteners, mechanical fasteners, or the like. In one aspect of the invention, the fastening system includes mechanical fastening elements for improved performance. Suitable mechanical fastening elements can be provided by interlocking geometric-shaped materials, such as hooks, loops, bulbs, mushrooms, arrowheads, balls on stems, male and female mating components, buckles, snaps, or the like.

Leg elastics 40 may extend around the leg openings 36 and 38 of the training pants 10, as representatively illustrated in FIG. 1, so as to provide gaskets for reducing or preventing leakage around the leg openings, between the training pants 10 and the legs of the wearer. Likewise, the training pants 10 may also include waist elastics 55. The waist elastics and the leg elastics 55 and 40 may be formed of any suitable elastic material that is well known to those skilled in the art. For example, suitable elastic materials include sheets, strands or ribbons of natural rubber, synthetic rubber, or thermoplastic elastomeric polymers. In one aspect of the invention, the waist elastics and/or the leg elastics may include a plurality of dry-spun coalesced multi-filament spandex elastomeric threads sold under the trade name LYCRA and available from Invista of Wilmington, Del., U.S.A.

The training pants 10 may also include containment flaps 42 adjacent the elasticized leg cuffs 40 for improved containment of liquid body exudates. Suitable constructions and arrangements for the containment flaps 42 are generally well known to those skilled in the art and are described, for example, in U.S. Pat. No. 4,704,116 issued on Nov. 3, 1987 to Enloe, the contents of which are incorporated herein by reference.

The outer cover 24 suitably includes a material that is substantially liquid impermeable. The outer cover 24 can be a single layer of liquid impermeable material, but more suitably includes a multi-layered laminate structure in which at least one of the layers is liquid impermeable. For instance, the outer cover 24 can include a liquid permeable outer layer and a liquid impermeable inner layer that are suitably joined together by a laminate adhesive, ultrasonic bonds, thermal bonds, or the like. The liquid permeable outer layer can be any suitable material and desirably is one that provides a generally cloth-like texture, for example a 20 grams per square meter (gsm) spunbond polypropylene nonwoven web. The inner layer of the outer cover 24 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 24 when a single layer, prevents waste material from wetting articles, such as bed sheets and clothing, as well as the wearer and caregiver. One example of a liquid impermeable film for use as a liquid impermeable inner layer, or a single layer liquid impermeable outer cover 24, is a 0.02 millimeter polyethylene film commercially available from Pliant Corporation of Schaumburg, Ill., U.S.A.

More suitably, the outer cover 24 is stretchable, and even more suitably the outer cover is elastic. For example, the outer cover 24 may be constructed of a single layer, multiple layers, laminates, films, nonwoven fabrics, elastic netting, microporous webs, bonded carded webs or foams comprised of elastomeric or polymeric materials. The materials may be extensible or stretchable in one direction or they may be biaxially extensible or stretchable. Elastomeric non-woven laminate webs can include a non-woven material joined to one or more gatherable non-woven webs, films, or foams. Stretch Bonded Laminates (SBL) and Neck Bonded Laminates (NBL) are examples of elastomeric composites. A non-woven fabric is any web of material that has been formed without the use of a textile weaving process that produces a structure of individual fibers that are interwoven in an identifiable repeating manner.

Examples of suitable materials are spunbond-meltblown fabrics, spunbond-meltblown-spunbond fabrics, spunbond fabrics, or laminates of such fabrics with scrims, films, foams, or other non-woven webs. Elastomeric materials may include cast or blown films, foams, or meltblown fabrics composed of polyethylene, polypropylene, or polyolefin copolymers, as well as combinations thereof. The elastomeric materials may include PEBAX® elastomer (available from AtoChem located in Philadelphia, Pa., U.S.A.), HYTREL® elastomeric polyester (available from E.I. DuPont de Nemours of Wilmington, Del., U.S.A.), KRATON® elastomer (available from Kraton Polymers of Houston, Tex., U.S.A.), or strands of LYCRA® elastomer (available from Invista of Wilmington, Del., U.S.A.), or the like, as well as combinations thereof. The outer cover 24 may include materials that have elastomeric properties through a mechanical process, printing process, heating process, or chemical treatment. For example, such materials may be apertured, creped, neck-stretched, heat activated, embossed, and/or micro-strained; and may be in the form of films, webs, and/or laminates.

In one aspect of the invention, the outer cover 24 may include a 13.6 gsm basis weight layer of G2760 KRATON elastomer strands adhesively laminated with a 0.3 gsm layer of adhesive to at least one facing. The facing can be composed of a thermal point bonded bicomponent spunbond non-woven fibrous web having a 23.7 gsm basis weight.

The bodyside liner 22 is suitably compliant, soft-feeling, and non-irritating to the wearer's skin. The bodyside liner 22 is also sufficiently liquid permeable to permit liquid body exudates such as urine to readily penetrate through its thickness to the temperature change member 12. A suitable bodyside liner 22 may be manufactured from a wide selection of web materials, such as porous foams, reticulated foams, apertured plastic films, woven and non-woven webs, or a combination of any such materials. For example, the bodyside liner 22 may include a meltblown web, a spunbonded web, or a bonded-carded-web composed of natural fibers, synthetic fibers or combinations thereof. The bodyside liner 22 may be composed of a substantially hydrophobic material, and the hydrophobic material may optionally be treated with a surfactant or otherwise processed to impart a desired level of wettability and hydrophilicity.

The bodyside liner 22 may also be stretchable, and more suitably it may be elastic. Elastomeric materials suitable for constructing the bodyside liner 22 include elastic strands, LYCRA elastics, cast or blown elastic films, nonwoven elastic webs, meltblown or spunbond elastomeric fibrous webs, as well as combinations thereof. Examples of suitable elastomers include KRATON elastomers, HYTREL elastomers, ESTANE elastomeric polyurethanes (available from B.F. Goodrich and Company of Cleveland, Ohio, U.S.A.), or PEBAX elastomers.

The bodyside liner 22 and the outer cover 24 may be attached to one another along at least a portion of their periphery by adhesive, ultrasonic bonding, thermal bonding or other suitable attachment means known in the art.

The absorbent assembly 25 is suitably compressible, conformable and capable of absorbing and retaining liquid body exudates released by the wearer. For example, the absorbent assembly can include a matrix of hydrophilic fibers, and more suitably cellulosic fluff, such as wood pulp fluff, and superabsorbent particles. One suitable pulp fluff is identified with the trade designation CR1654, commercially available from U.S. Alliance, Childersburg, Ala., U.S.A., and is a bleached, highly absorbent sulfate wood pulp containing primarily soft wood fibers and about 16% hardwood fibers. As an alternative to wood pulp fluff, synthetic fibers, polymeric fibers, meltblown fibers, short cut homofil bicomponent synthetic fibers, or other natural fibers may be used. Suitable superabsorbent materials can be selected from natural, synthetic, and modified natural polymers and materials. The superabsorbent materials can be inorganic materials, such as silica gels, or organic compounds, such as crosslinked polymers, for example, sodium neutralized polyacrylic acid. Suitable superabsorbent materials are available from various commercial vendors, such as Dow Chemical Company of Midland, Mich., U.S.A., and Stockhausen Inc., Greensboro, N.C., U.S.A.

The absorbent assembly 25 can have a density within the range of about 0.10 to about 0.5 grams per cubic centimeter and may be wrapped or encompassed by a suitable tissue or nonwoven wrap for maintaining the integrity and/or the shape of the absorbent assembly.

In some aspects, a surge management layer (not shown) may be located adjacent the absorbent assembly 25, for example between the absorbent assembly 25 and the bodyside liner 22, and attached to one or more components of the chassis 14 by methods known in the art, such as by adhesive, ultrasonic or thermal bonding. A surge management layer helps to decelerate and diffuse surges or gushes of liquid that may be rapidly introduced into the absorbent assembly 25. Desirably, the surge management layer can rapidly accept and temporarily hold the liquid prior to releasing the liquid into the storage or retention portions of the absorbent assembly 25. Examples of suitable surge management layers are described in U.S. Pat. Nos. 5,486,166 and 5,490,846, the contents of which are incorporated herein by reference.

The absorbent assembly 25 may have a variety of shapes and configurations that may assist with the performance of the temperature change member 12. For example, as representatively illustrated in FIGS. 2 and 7, the absorbent assembly 25 may include an absorbent assembly front portion 26 and an absorbent assembly rear portion 26 disposed intermediate the outercover 22 and the bodyside liner 24. The absorbent assembly front portion 26 may be at least partially spaced from the absorbent assembly rear portion 28 to define a first gap indicated by the arrow marked C. That is, the first gap C may be provided by the spacing between the inner edge of the absorbent assembly front portion 26 and the inner edge of the absorbent assembly rear portion 28. In a particular aspect, the absorbent assembly front portion 26 may be completely spaced from the absorbent assembly rear portion 28, as representatively illustrated in FIG. 2. For example and as will be described in greater detail below, such a configuration may be accomplished by disposing the absorbent assembly 25 in a spaced manner between the liner 22 and the outercover 24.

Alternatively, as representatively illustrated in FIG. 7, the absorbent assembly front portion 26 may only be partially spaced from the absorbent assembly rear portion 28. That is, the first gap C need not extend across the entire width of the absorbent assembly 25 in the crotch region 20 of the pants 10. For example, the absorbent assembly 25 may include an absorbent assembly central portion 70 in the crotch region 20 of the pants 10 located between the absorbent assembly front portion 26 and the absorbent assembly rear portion 28. In particular, a portion of the absorbent assembly 25, such as one or more strips 80 may extend through the crotch region 20 and connect the absorbent assembly front portion 26 to the absorbent assembly rear portion 28 to provide the absorbent assembly central portion 70 (FIG. 7). As such, the first gap C may be provided by an opening within the absorbent assembly central portion 70. Such a configuration may be accomplished by forming an absorbent assembly 25 with first gap C in the central portion 70, or first gap C may be provided subsequent to the formation of absorbent assembly 25, such as by cutting out and removing a portion of the absorbent assembly central portion 70. In one aspect, a water cutter may be used to cut out and remove a portion of the absorbent assembly central portion 70.

As can be appreciated by one of ordinary skill in the art, the first gap C may be a variety of shapes and sizes. For example, in the illustrated aspects, the first gap C may be generally rectangular in shape. Alternatively, the first gap C may be oval, circular, triangular, and the like or combinations thereof. Further, in the various aspects of the present invention the first gap C is generally free of highly absorbent material such as cellulose fluff and superabsorbent material, but may include a tissue layer or a nonwoven wrapsheet layer.

Turning now to FIG. 2, the absorbent assembly front portion 26 may be disposed in the front region 16 of the training pants 10, intermediate the outercover 22 and the liner 24. For example, the absorbent assembly front portion may be attached to the outer cover 24 or the liner 22. Similarly, the absorbent assembly rear portion may be disposed in the rear region 18 of the training pants 10, intermediate the outercover 24 and the liner 22. For example, the absorbent assembly rear portion 28 may be attached to the outer cover 24 or the liner 22. The temperature change member 12 may then be disposed in the crotch region 20 of the training pants 10, between the absorbent assembly front portion 26 and the absorbent assembly rear portion 28. As such, upon insult, the urine may more effectively interact with the temperature change member 12 thereby resulting in a more noticeable temperature change for the wearer. For example, the temperature change member 12 may be attached to the outercover 24 or the liner 22.

In one aspect of the invention, the absorbent assembly front portion 26 is the same size as the absorbent assembly rear portion 28, and hence the length A of the absorbent assembly rear portion 28 is the same as the length B of the absorbent assembly front portion 26. Suitably, the absorbent assembly front portion and rear portion 26 and 28 are disposed on the chassis 14 such that the length of the first gap C can be equal to the sum of a second gap and a third gap. The second gap is provided by the spacing between the outer edge of the absorbent assembly front portion 26 and a front waist edge 44 and is indicated by the arrow marked D; the third gap is the distance between the outer edge of the absorbent assembly rear portion 28 and a rear waist edge 46 and is indicated by the arrow marked E. This configuration of the absorbent assembly first portion and second portion 26 and 28 provides advantages in the production of training pants according to the present invention. For example, with this configuration, the absorbent assemblies 26 and 28 may be cut from the same roll of absorbent material and may be applied continuously to a web for forming training pants according to aspects of the present invention.

Figure 3:
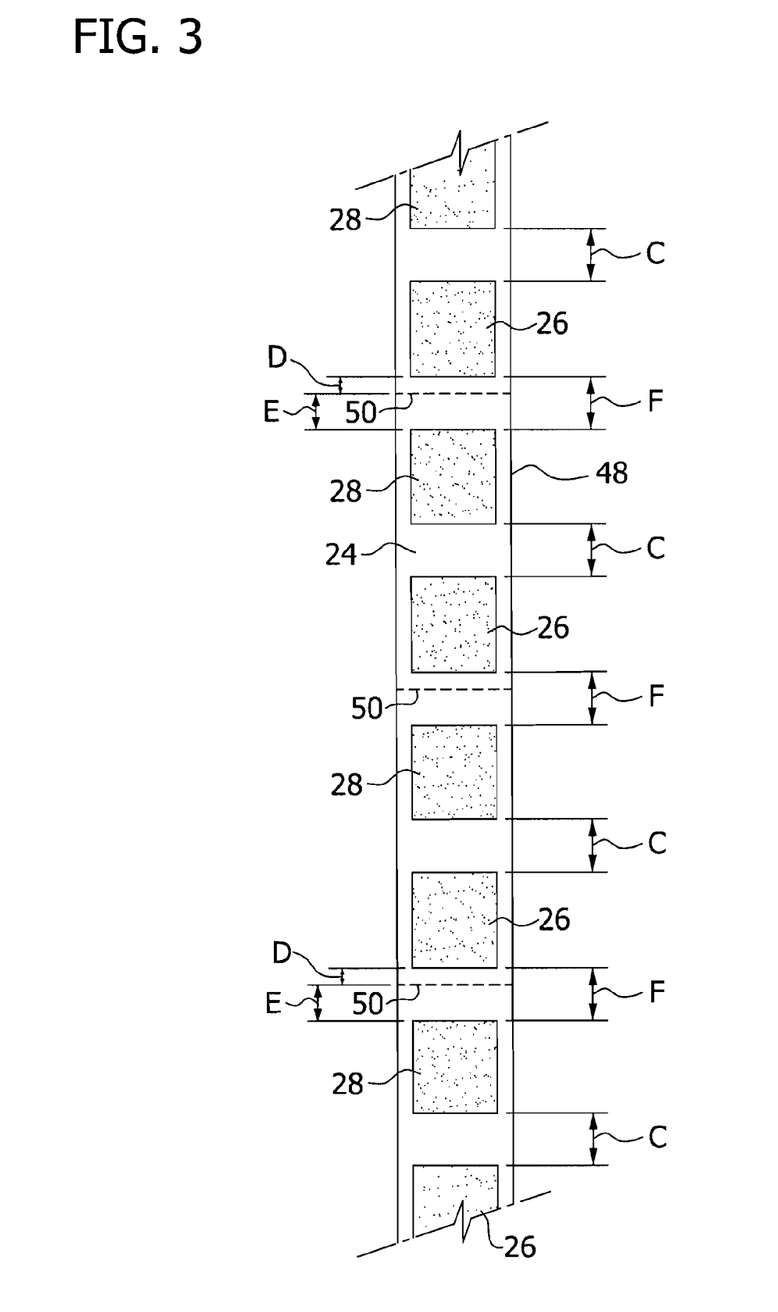
FIG. 3 representatively illustrates a top view of a portion of a web for forming absorbent articles according to the present invention.

FIG. 3 illustrates a portion of a web 48 of outer cover material for forming training pants according to aspects of the present invention in an automated process. The absorbent assembly front portion and rear portion 26 and 28 may be formed by unwinding absorbent material from a supply roll (not illustrated), cutting the absorbent material at regular intervals, and applying the absorbent material to the web 48 at regular intervals to form alternating absorbent assembly front and rear portions 26 and 28, which are spaced from one another by first gap C and a fourth gap, which is indicated by the arrow marked F. Suitably, the length of the fourth gap F is the substantially the same as the first gap C. Accordingly, the web 48 may be cut along the broken lines 50, thereby traversing the fourth gap F and forming individual training pants 10. Thus, the fourth gap F can be divided into the second gap and the third gap D and E, which together may be the same length as the first gap C.

The supply roll may be driven by a variable speed drive (not shown), that may be adjusted to effect suitable unwinding of the absorbent material. Any suitable cutting device may be used to cut the absorbent material. For example, the absorbent material may be cut by a mechanical pinch-type cut-off knife, a shear-type cut-off knife, a hot knife, or other cutting means well known in the art. As mentioned above, the absorbent assembly 25 may optionally be attached to the web 48 by any suitable means such as, for example, adhesive bonding. Suitable adhesives include spray adhesives, hot-melt adhesives, self-adhering elastomeric materials and the like, which may be obtained from Bostik Findley Adhesives, Inc., of Wauwatosa, Wis., U.S.A., or from National Starch and Chemical Company, of Bridgewater, N.J., U.S.A.

Figure 4:
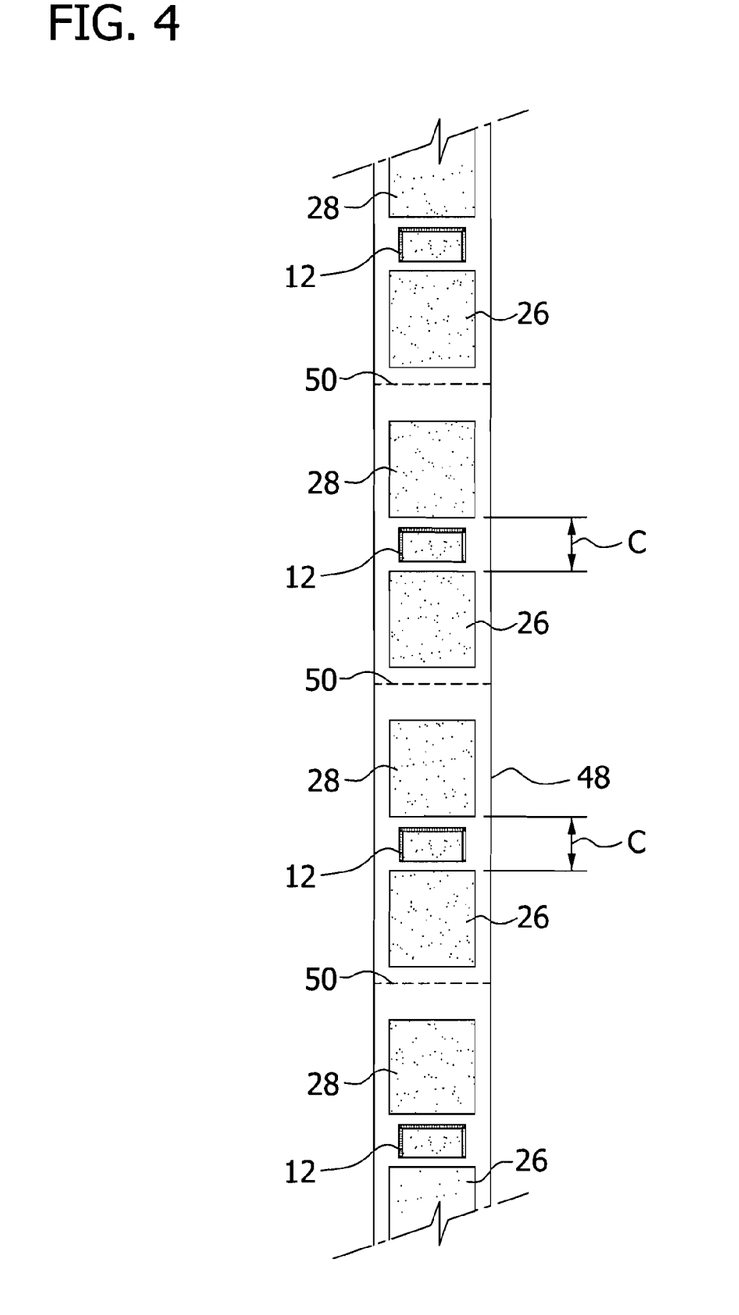
FIG. 4 representatively illustrates a top view similar to that of FIG. 3 with the web at a further stage in the production.

FIG. 4 representatively illustrates a subsequent stage in the production of training pants according to one aspect of the invention in which temperature change members 12 have been disposed on the web 48 in alternate gaps (i.e., the first gap C) between the front and rear absorbent assemblies 26 and 28. Accordingly, when the web 48 is cut along the broken lines 50 to form separate training pants 10, each pants can include an absorbent assembly front portion 26, an absorbent assembly rear portion 28 and a temperature change member 12 disposed in the first gap C between the absorbent assembly front and rear portion 26 and 28.

Figure 5:
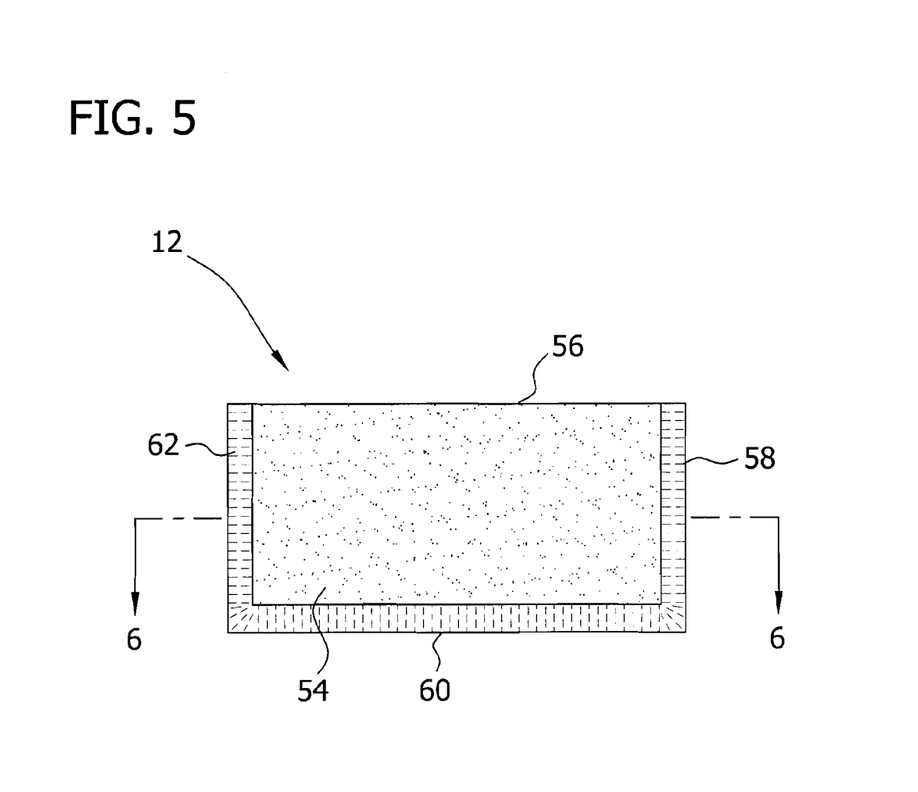
FIG. 5 representatively illustrates a top view of an example of a temperature change member for an absorbent article according to the present invention.
Figure 6:
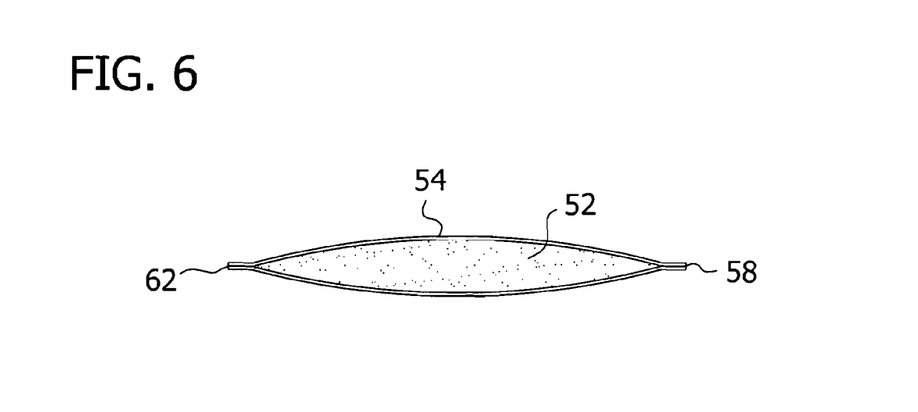
FIG. 6 representatively illustrates a cross-sectional view along the line 6-6 in FIG. 5.

The temperature change member 12 is adapted to create a distinct temperature change sensation upon urination. With reference to FIGS. 5 and 6, this temperature change sensation results from a temperature change substance 52 that may include particles captured within a holder 54. In one aspect of the invention, the holder 54 may include a containment pouch formed from a sheet of material that is folded over the temperature change substance 52 along a fold line 56 and bonded along edges 58, 60 and 62 to enclose the temperature change substance within the pouch. The edges of the material sheet may be bonded together by any suitable means such as, for example, sonic bonds, thermal bonds, adhesive bonds, and the like. Alternatively, the temperature change substance 52 may be contained between two layers of material that are joined together along all of the side edges thereof, or within various other types of suitable holders.

The holder 54 may be formed from a highly wettable non-woven material such as a co-form. In one aspect of the invention, the sheet of co-form may include a sheet of NSP 130 gsm, 2.4 mm bulk, 65:35 fluff/polypropylene ratio co-form. Various co-form materials are known to those skilled in the art. For instance, examples of co-form materials are described in U.S. Pat. No. 4,100,324, issued Jul. 11, 1978, to Anderson, et al., the contents of which are hereby incorporated herein by reference.

Alternatively, the holder 54 may include a porous film or fibrous layer. The fibrous layer may include a fibrous tissue, a woven or non-woven fabric, a cellulosic fibrous web, or the like. Suitable holders may be formed, for example, from a liquid-permeable web material, such as a liquid-permeable film, tissue, fabric, or the like. The fabric may be composed of a hydrophilic material or composed of a hydrophobic material that has been suitably treated to render it sufficiently hydrophilic.

The temperature change substance 52 can include a material that provides a temperature change when placed near the wearer and contacted with urine. The temperature change can be either an absorption or release of heat that is noticeable to the wearer. Absorption of heat by the temperature change substance 52 will provide the wearer with a cool sensation, while a release of heat by the substance will provide the wearer with a warm sensation. Reference is made to aforementioned U.S. patent application Ser. No. 10/462,166, in the name of Olson, et al., incorporated by reference herein, for additional information regarding the mechanism by which the temperature change sensation is accomplished.

The temperature change substance 52 is responsive to contact with an aqueous solution such as urine to either absorb or release heat. The mechanism by which this is accomplished is dissolution of the substance in the aqueous solution, swelling of the substance in the aqueous solution, or reaction of the substance in the aqueous solution. For example, the temperature change substance may include particles that have a substantial energy difference between a dissolved state and a crystalline state so that energy in the form of heat is absorbed or released to the environment upon contact with urine, or the temperature change substance may release or absorb energy during swelling or reacting in an aqueous solution.

While a wide variety of substances may result in a temperature change when contacted with an aqueous solution, the selection of a particular temperature change substance 52, the determination of the amount to be used and the location of the substance should be based in part on the desired temperature change. Specifically, the temperature change member 12 may suitably provide the training pants 10 with a temperature change of at least about 5° C., more suitably about 10° C., still more suitably about 15° C., and still yet more suitably about 20° C. when wet. As a result, in aspects where the temperature change substance is endothermic, a drop in the temperature of the product when insulted can be from about 37° C. to about 25° C., and further to about 20° C., and still further to about 16° C. The temperature change can suitably last for at least 10 minutes, and more suitably for approximately 15 minutes. Further, in the case of an endothermic temperature change substance 52, the temperature change can suitably lower (at least temporarily) the temperature of the training pants 10 to less than about 25° C. for improved effectiveness, particularly with a preoccupied wearer (i.e., a playing child).

By way of example, Xylitol particles may be selected to provide a cooling sensation because Xylitol particles absorb heat when dissolved in an aqueous solution. Other suitable temperature change substances that absorb heat during dissolution include salt hydrates, such as sodium acetate ($H_2O$), sodium carbonate ($10H_2O$), sodium sulfate ($10H_2O$), sodium thiosulfate ($5H_2O$), and sodium phosphate ($10H_2O$); anhydrous salts such as ammonium nitrate, potassium nitrate, ammonium chloride, potassium chloride, and sodium nitrate; organic compounds such as urea or the like. Temperature change substances that release heat during dissolution include aluminum chloride, aluminum sulfate, potassium aluminum sulfate, or the like.

The temperature change substance 52 may also include those substances that absorb or release heat during swelling. By way of illustration, one suitable temperature change substance that releases heat during swelling is a lightly cross-linked partially neutralized polyacrylic acid.

Alternatively, the temperature change substance may include those substances that absorb or release heat upon reaction with an aqueous solution. Examples include ortho esters or ketals such as menthone ketals that result from reacting menthone with alcohols containing 1 to 8 carbons or polyols containing 2 to 8 carbons, and all structural and optical isomers thereof. Particular menthone ketals that may be suitable include menthone-glycerol ketal and menthone-propylene glycol ketal. Particular ketals are disclosed in U.S. Pat. No. 5,348,750 issued to Greenberg, and U.S. Pat. No. 5,266,592 issued to Grub et al.

Thus, as described above, the holder 54 may be formed from a co-form material, and the temperature change substance 52 may include Xylitol particles contained within the co-form holder. Once wet by urination, the Xylitol dissolves, creating an endothermic response, and the high re-wet co-form holder 54 remains wet, cold and soggy, thereby signaling to the wearer that urination has occurred.

The temperature change member 12 is disposed within the training pants 10 so that, upon urination, liquid makes contact with the temperature change substance 52. More specifically, the temperature change member 12 may be disposed in the first gap C. For example, the temperature change member 12 can be disposed intermediate the outercover 24 and liner 22 in the first gap C between the absorbent assembly front portion 26 and the absorbent assembly rear portion 28. Accordingly, liquid passing through the bodyside liner 22 can collect between the absorbent assemblies 26 and 28, interact with the temperature change substance 52 and cool down, before the urine is absorbed by the absorbent assembly 25. In one aspect, the temperature change member disposed in the first gap C may further be spaced from the absorbent assembly front portion 26 and the absorbent assembly rear portion 28. In addition, the containment flaps 42 can serve to improve the gathering of liquid in the crotch region 20 of the training pants 10. Thus, the collection of liquid allows for a relatively high temperature change, for example a drop in temperature of urine from about 37° C. to about 25° C., and further to about 20° C., and still further to about 16° C., for signaling urination to the wearer. In practice, urine collecting between the front and rear absorbent assemblies will gradually be absorbed into the absorbent assemblies with body movements of the wearer.

As can be readily appreciated, the temperature change member 12 can be of various shapes and sizes. For example, the temperature change member 12 may be rectangular and may measure about 8 cm by about 10 cm. Alternatively, the temperature change member 12 can be oval in shape, circular, triangular, or the like. Further, the temperature change member 12 can suitably contain various amounts of the temperature change substance 52. For example, in the case of Xylitol, the temperature change member 12 can contain between about 5 grams and about 30 grams, and particularly between about 10 grams and about 25 grams, for example about 17 grams. Further, it will be understood by those of skill in the art that the training pants 10 of the present invention could include more than one temperature change member 12 between the absorbent assembly front portion and rear portion 26 and 28.

By configuring the temperature change member 12 and the absorbent assembly 25 in accordance with the present invention, training pants 10 can be produced with enhanced temperature change capability. Since the liquid contacting the temperature change member 12 is allowed to collect between the absorbent assembly front portion and rear portion 26 and 28, it may more readily interact with the temperature change material 52 before it is absorbed by the absorbent assembly 25. Thus, a greater degree of temperature change sensation and a greater signal of urination, can be achieved. In addition, the configuration of the temperature change member 12 and the absorbent assembly 25 allows for a relatively thin garment, which enhances the underwear-like perception of the training pants 10. Finally, the configuration of the various components in accordance with the present invention can facilitate the automated production of the training pants 10.

A suitable procedure for determining the temperature change when wet of a product containing a temperature change substance is described below in the temperature change test as follows. The test should be conducted in an environment having a stable temperature of 21° C. to 22° C. and a stable humidity of about 50 percent. The product to be tested is prepared by removing any elastic side panels and cutting all other elastics to permit the product to lay as flat as possible. The product is positioned in a Plexiglas cradle to simulate the configuration of the product in actual use. The center of the product is placed in the deepest portion of the cradle.

A liquid dispensing nozzle operatively connected to a liquid dispensing pump is positioned to dispense saline onto the inner surface of the product. The tip of the nozzle should be located 1 cm away from the inner surface and 10 cm forward of the center of the product, along the product's longitudinal axis. The pump is activated to dispense 90 ml of a stabilized isotonic 0.9% saline at a rate of 15 ml/sec. The saline is certified blood bank saline available from The Baxter Healthcare Corporation, Scientific Products Division, McGraw Park, Ill., and is at a temperature of 37° C.

The surface temperature of the product at the location of the temperature change substance is measured using a standard thermometer or temperature sensing thermistors connected to a digital display or recording device. The surface temperature 30 seconds after the saline is dispensed is recorded as the test temperature. A reference temperature is obtained by performing this test on a portion of the product not including the temperature change substance or on a similar product without the temperature change substance. The surface temperature change when wet for the product is the difference between the test temperature and the reference temperature.

While the invention has been described in detail with respect to specific embodiments thereof, it will be appreciated that those skilled in the art, upon attaining an understanding of the foregoing, may readily conceive of alterations to, variations of and equivalents to these embodiments. Accordingly, the scope of the present invention should be assessed as that of the appended claims and any equivalents thereto.

What is claimed is:

1. An absorbent article defining a front waist edge, a rear waist edge, a front region, a rear region, and a crotch region intermediate the front and rear regions, the absorbent article comprising:
    a liquid impermeable outer cover;
    an absorbent assembly having a front portion and a rear portion;
    the absorbent assembly front portion being disposed on the outer cover in the front region;
    the absorbent assembly rear portion being disposed on the outer cover in the rear region and at least partially spaced from the absorbent assembly front portion to provide a first gap; and
    a temperature change member disposed on the outer cover in the first gap,
    the length of the absorbent assembly front portion being the same as the length of the absorbent assembly rear portion, and the length of the first gap between the absorbent assembly front portion and the absorbent assembly rear portion being the same as the sum of:
    (a) the length of a second gap between the absorbent assembly front portion and the front waist edge; and
    (b) the length of a third gap between the absorbent assembly rear portion and the rear waist edge.

2. The absorbent article of claim 1, wherein the temperature change member is spaced from the front portion of the absorbent assembly and the rear portion of the absorbent assembly.

3. The absorbent article of claim 1, wherein the temperature change member provides the article with a temperature change of at least about 50° C.

4. The absorbent article of claim 3, wherein the temperature change member provides the article with a temperature change of at least about 10° C.

5. The absorbent article of claim 1, wherein the temperature change member contains a temperature change substance and wherein the temperature change substance is an endothermic material.

6. The absorbent article of claim 5, wherein the endothermic material is Xylitol.

7. The absorbent article of claim 1, wherein the temperature change member contains a temperature change substance and wherein the temperature change substance is an exothermic material.

8. The absorbent article of claim 1, wherein the temperature change member comprises a holder and wherein the holder is formed from a wettable, non-woven material.

9. The absorbent article of claim 8, wherein the wettable non-woven material is a co-form.

10. The absorbent article of claim 1, further comprising a pair of containment flaps.

11. An absorbent article having a front region, a rear region, and a crotch region extending longitudinally between and interconnecting the front and rear regions, the absorbent article comprising:
    a liquid impermeable outer cover;
    a liquid permeable bodyside liner;
    an absorbent assembly having a front portion, a rear portion, and a central portion extending longitudinally between and interconnecting the front portion and rear portion, wherein the length of the front portion is the same as the length of the rear portion: the central portion having an opening therein to define a gap between the front portion and the rear portion;
    the absorbent assembly front portion being disposed intermediate the outer cover and the liner in the front region of the article;
    the absorbent assembly rear portion being disposed intermediate the outer cover and the liner in the rear region of the article; and
    a temperature change member containing a temperature change substance, said temperature change substance being disposed in the opening of the central portion of the assembly and on the outer cover.

12. The absorbent article of claim 11 wherein the temperature change member is free from contact with the absorbent assembly front portion and the absorbent assembly rear portion, said temperature change member being spaced longitudinally from each of the absorbent assembly front portion and the absorbent assembly rear portion.

13. The absorbent article of claim 11 further comprising a front waist edge and a rear waist edge, the absorbent assembly front portion being spaced from the front waist edge by a second gap, and the absorbent assembly rear portion being spaced from the rear waist edge by a third gap.

14. The absorbent article of claim 11, further defining a front waist edge and a rear waist edge, the length of the first gap between the absorbent assembly front portion and the absorbent assembly rear portion being the same as the sum of:
    (a) the length of a second gap between the absorbent assembly front portion and the front waist edge; and
    (b) the length of a third gap between the absorbent assembly rear portion and the rear waist edge.

15. The absorbent article of claim 11 wherein the temperature change member is spaced from the absorbent assembly front portion and the absorbent assembly rear portion.

16. The absorbent article of claim 11, wherein the temperature change member provides the article with a temperature change of at least about 50° C.

17. The absorbent article of claim 16, wherein the temperature change member provides the article with a temperature change of at least about 10° C.

18. The absorbent article of claim 11, wherein the temperature change substance is an endothermic material.

19. The absorbent article of claim 18, wherein the endothermic material is Xylitol.

20. The absorbent article of claims 11, wherein the temperature change subtance is an exothermic material.

21. The absorbent article of claim 11, wherein the temperature change substance is contained within a holder that is formed from a liquid permeable material in at least a portion thereof.

22. The absorbent article of claim 21, wherein the holder is formed from a wettable, non-woven material.

23. The absorbent article of claim 22, wherein the wettable nonwoven material is a co-form.

24. The absorbent article of claim 11, further comprising a pair of containment flaps.

25. The absorbent article of claim 11, wherein the article is a disposable training pant.

* * * * *

UNITED STATES PATENT AND TRADEMARK OFFICE
CERTIFICATE OF CORRECTION

PATENT NO. : 7,250,548 B2
APPLICATION NO. : 10/955534
DATED : July 31, 2007
INVENTOR(S) : Weber et al.

It is certified that error appears in the above-identified patent and that said Letters Patent is hereby corrected as shown below:

In Claim 3, column 13, line 43, delete "at least about 50° C." and insert therefor -- at least about 5° C. --.
In Claim 16, column 14, line 46, delete "at least about 50° C." and insert therefor -- at least about 5° C. --.

Signed and Sealed this

Twenty-seventh Day of November, 2007

JON W. DUDAS
*Director of the United States Patent and Trademark Office*